(12) United States Patent
Suau et al.

(10) Patent No.: US 7,956,211 B2
(45) Date of Patent: Jun. 7, 2011

(54) TRITHIOCARBONATE DERIVATIVES AND THE USE THEREOF IN THE FORM OF TRANSFER AGENTS FOR ACRYLIC ACID CONTROLLED RADICAL POLYMERISATION

(75) Inventors: Jean-Marc Suau, Lucenay (FR); Christian Jacquemet, Lyons (FR)

(73) Assignee: Coatex S.A.S., Genay (FR)

( * ) Notice: Subject to any disclaimer, the term of this patent is extended or adjusted under 35 U.S.C. 154(b) by 1070 days.

(21) Appl. No.: 10/594,520

(22) PCT Filed: Mar. 23, 2005

(86) PCT No.: PCT/FR2005/000702
§ 371 (c)(1),
(2), (4) Date: Sep. 28, 2006

(87) PCT Pub. No.: WO2005/095466
PCT Pub. Date: Oct. 13, 2005

(65) Prior Publication Data
US 2007/0179262 A1   Aug. 2, 2007

(30) Foreign Application Priority Data
Mar. 29, 2004 (FR) ..................... 04 03197

(51) Int. Cl.
*C07C 327/36* (2006.01)
(52) U.S. Cl. ...................................... 558/243
(58) Field of Classification Search ............... None
See application file for complete search history.

(56) References Cited

U.S. PATENT DOCUMENTS
2004/0097674 A1   5/2004   Suau et al.
2006/0111534 A1   5/2006   Suau et al.

FOREIGN PATENT DOCUMENTS
| DE | 217 214 A1 | 1/1985 |
| WO | 01/60792 | 8/2001 |
| WO | 02/070571 | 9/2002 |
| WO | 03/055919 | 7/2003 |

OTHER PUBLICATIONS

Wetterholm, N,N'Bis(B,BB-trinitroethyl)urea, Svensk Kemisk Tidskrift (1964), 76(11), pp. 628-634. CAPlus AN 1965:66084. and 6332-91-8 Registry.*
Mayadunne, Roshan T. A. et al., "Living Polymers by the Use of Trithiocarbonates as Reversible Addition-Fragmentation Chain Transfer (RAFT) Agents: ABA Triblock Copolymers by Radical Polymerization in Two Steps", Macromolecules, vol. 33, No. 2, pp. 243-245, 2000.
Lai, John T. et al., "Functional Polymers from Novel Carboxyl-Terminated Trithiocarbonates as Highly Efficient RAFT Agents", Macromolecules, vol. 35, No. 18, pp. 6754-6756, 2002.
U.S. Appl. No. 10/594,519, filed Sep. 28, 2006, Suau, et al.

* cited by examiner

*Primary Examiner* — Yong Chu
*Assistant Examiner* — Michael Barker
(74) *Attorney, Agent, or Firm* — Oblon, Spivak, McClelland, Maier & Neustadt, L.L.P.

(57) ABSTRACT

The invention relates to novel sulphur compounds, to the production thereof by a method carried out in an aqueous medium and the use thereof in the form of transfer agents in a method for controlled radical polymerization of acrylic acid and/or acrylic acid with water-soluble monomers in water. The thus obtained polymers are usable in the form of dispersing agents or grinding aid agents and/or aid agents for combined grinding of mineral materials in an aqueous suspension and in the form of dispersing agents directly incorporated into aqueous formulations containing mineral materials.

7 Claims, No Drawings

TRITHIOCARBONATE DERIVATIVES AND THE USE THEREOF IN THE FORM OF TRANSFER AGENTS FOR ACRYLIC ACID CONTROLLED RADICAL POLYMERISATION

The present invention concerns the field of processes for controlled radical polymerisation of the RAFT (Reversible Addition Fragmentation Transfer) type of homopolymers of acrylic acid and/or copolymers of acrylic acid with other water-soluble monomers.

Firstly, the invention concerns compounds characterised in that they have a chemical structure in accordance with the following formula (I):

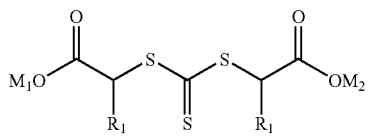

where $R_1$ designates an alkyl radical having 2 to 10 carbon atoms, an aromatic radical possibly substituted by an alkyl chain having 1 to 4 carbon atoms;

and where $M_1$ and $M_2$ designate the hydrogen atom, an amine salt, ammonium or an alkaline cation, and are identical or different.

The invention also concerns a process for manufacturing the said compounds of formula (I) in water, by:

a) Bringing into contact by pouring an aqueous solution of disodic trithiocarbonate $Na_2CS_3$ or an aqueous solution of dipotassic trithiocarbonate $K_2CS_3$ on a solution of a halogenated salt, which salt has a chemical structure in accordance with the following formula (II):

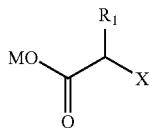

where $R_1$ designates an alkyl radical having 2 to 10 carbon atoms, an aromatic radical possibly substituted by an alkyl chain having 1 to 4 carbon atoms;

where M designates ammonium, or an alkaline cation such as sodium, potassium or lithium;

where X designates a halogen.

b) and possibly a stage of acidification of the compound after stage a).

The invention also concerns the use, as transfer agents in a process of controlled radical polymerisation of the RAFT type, in water, of homopolymers of acrylic acid and/or copolymers of acrylic acid with other water-soluble monomers, of compounds having the following formula (I'):

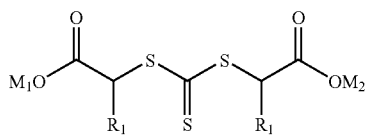

where $R_1$ designates an alkyl radical having 1 to 10 carbon atoms, a simple aromatic radical or one substituted by an alkyl chain having 1 to 4 carbon atoms;

and where $M_1$ and $M_2$ designate the hydrogen atom, an amine salt, ammonium or an alkaline cation, and are identical or different.

The invention also concerns the homopolymers of acrylic acid and/or copolymers of acrylic acid with other water-soluble monomers, obtained by the said process and characterised in that they have a polydispersity index lower than 2.2 and contain at the end of the chain a pattern which is in accordance with the following formula (III):

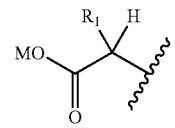

where $R_1$ designates an alkyl radical having 1 to 10 carbon atoms, an aromatic radical possibly substituted by an alkyl chain having 1 to 4 carbon atoms;

and where M designates the hydrogen atom, an amine salt, ammonium or an alkaline cation.

The MALDI TOF method enables the presence of the pattern of formula (III) at the end of the polymer chain according to the invention to be demonstrated. This method is a technique for time of flight analysis by mass spectrometry which is well known by the skilled man in the art ("Controlled radical polymerization of acrylic acid in protic media", Macromolecules, 2001, 34, 5370 and "Synthesis and characterization of poly(acrylic acid) produced by RAFT polymerization: application as a very efficient dispersant of CaCO3, kaolin, and TiO2", Macromolecules, 2003, 36, 3066).

The invention also concerns the use as grinding aid and/or co-grinding aid agent of mineral matter in water, of the said homopolymers of acrylic acid and/or of the said copolymers of acrylic acid with other water-soluble monomers.

The invention also concerns the use as dispersing agent of mineral matter in water, of the said homopolymers of acrylic acid and/or of the said copolymers of acrylic acid with other water-soluble monomers.

The invention also concerns aqueous suspensions of mineral matter ground and/or co-ground with the polymers according to the invention.

The invention also concerns aqueous dispersions of mineral matter dispersed with the polymers according to the invention.

The invention also concerns the use of the said aqueous dispersions and suspensions of mineral matter, in paper formulations, and notably in coating colours and mass fillings, in paint, plastic, cement and ceramic formulations, in formulations for the treatment of water, detergent and cosmetic formulations, and in drilling muds.

The Applicant wishes to specify here that every dispersant used in the treatment of water also has an anti-scaling function.

He also stipulates that the use of the said aqueous dispersions and suspensions in plastic formulations involves a stage of drying of the said dispersions and suspensions, a stage which is well known by the skilled man in the art.

The invention also concerns the direct use, as dispersing agent, of homopolymers of acrylic acid and/or of copolymers of acrylic acid with other water-soluble monomers according to the invention, in paper formulations, and notably in coating colours and mass fillings, in paint, cement and ceramic formulations, in formulations for the treatment of water, in detergent and cosmetic formulations, and in drilling muds.

The invention also concerns paper formulations, and notably coating colours and mass fillings, paint, plastic, cement and ceramic formulations, formulations for the treatment of water, detergent and cosmetic formulations, and drilling muds, obtained through the use in the said formulations of the aqueous dispersions and suspensions of mineral matter according to the invention.

Finally, the invention concerns paper formulations, and notably coating colours and mass fillings, paint, plastic, cement and ceramic formulations, formulations for the treatment of water, detergent and cosmetic formulations, and drilling muds, obtained through the direct use as dispersing agent in the said formulations of the polymers according to the invention.

Homopolymers of acrylic acid, and copolymers of acrylic acid with water-soluble monomers, are now well known as products with multiple applications, notably in the field of aqueous suspensions and dispersions of mineral matter as dispersing agents or as grinding aid agents, but also as dispersing agents in the more general field of aqueous formulations such as, notably, those used in the paper field for the manufacture of coating colours or mass filling, or in the field of aqueous paints.

Obtaining such homopolymers and copolymers with a high conversion rate (notably higher than 90%) i.e. an optimum reaction yield, a low polydispersity index (notably lower than 2.2), a controlled molecular mass, i.e. the possibility for the manufacturer to obtain a molecular mass of their choice, is thus a matter of very great importance for the skilled man in the art.

To this end, it is common to use processes for controlled radical polymerisation (CRP: Controlled Radical Polymerization), whilst seeking to obtain the properties required for the homopolymers and copolymers thus obtained.

Among them, the first were ATRP (Atom Transfer Radical Polymerization) and NMP (Nitroxide Mediated Polymerization). It was nonetheless realised that they were not completely satisfactory. With ATRP, it was demonstrated in the document "Atom-transfer radical polymerization and the synthesis of polymeric materials" (Advanced Materials (1998), 10 (12), 901-915), that polymerisation of acrylic acid was difficult. Indeed, acrylic acid reacts rapidly with the catalyst, giving rise to compounds which do not enable the polydispersity index of the final product to be controlled effectively (see page 910). However, document FR 2 797 633 proposes a method for polymerisation of acrylic and methacrylic monomers by this means. However, these documents give rise to new problems for the skilled man in the art. Indeed, the ATRP process uses copper salt based catalysts which cause undesirable pollution; copper will be found again in the synthesised products, which the skilled man in the art does not necessarily desire. In the case of NMP, other work has shown that the acid grouping was involved in related reactions with nitroxides, leading to reaction by-products, as described in the document "Rate Enhancement of Living Free-Radical Polymerizations by an Organic Acid Salt" (Macromolecules (1995), 28(24), 8453-8455). In addition, in the case of the synthesis of polyacrylic acid using this technique, it was shown that the rate of conversion did not follow the degree of polymerisation ("Direct synthesis of controlled poly(styrene-co-acrylic acid)s of various compositions by nitroxide-mediated random copolymerization", Macromol. Chem. Phys. (2003), 204, 2055-2063): it is thus difficult to use this method to control precisely the degree of polymerisation of the acrylic acid.

The skilled man in the art then turned to another technique of controlled radical polymerisation: RAFT (Reversible Addition Fragmentation Transfer).

Initially processes of the RAFT type using transfer agents manufactured in solvents and polymers also synthesised in the presence of solvents were developed.

One is thus familiar with document EP 0 910 587 which describes a process for the manufacture of compounds of the general formula $Z(C=S)SR$, used as a chain transfer agent in processes of the RAFT type, and which teaches that it is necessary to choose an appropriate solvent in accordance with the monomers which one wishes to polymerise, as is shown notably by example 22, using dimethylformamide for the synthesis of polyacrylic acid. In addition, the Applicant notes that the rate of conversion is particularly low, since it is equal to 17.5%.

This approach has continued to be studied, and the skilled man in the art also now has the document "Controlled polymerization of acrylic acid under $^{60}Co$ irradiation in the presence of dibenzyl trithiocarbonate" (Journal of Polymer Science: Part A: Polymer Chemistry (2001), 39, 3934-3939). It describes the polymerisation of acrylic acid using the RAFT technique in the presence of dibenzyl trithiocarbonate, which is excited by irradiation at $^{60}Co$, and then diluted in dimethylformamide. In addition, the dibenzyl trithiocarbonate is prepared in the presence of a solvent which must be evaporated at the end of the reaction.

This type of process has the double disadvantage of using organic solvents, both during the manufacture of the transfer agent, and in the polymerisation stage. In addition to the fact that they may be dangerous for the user and harmful for the environment, these solvents must be eliminated at the end of the reaction to purify the product by evaporation, distillation, or any other means well known by the skilled man in the art: this makes the process longer and more costly. There is thus an essential need to find a solution to the problem of the refinement of processes no longer using organic solvents, both during the manufacture of the transfer agent and during synthesis by RAFT means of the polymers. The skilled man in the art is thus now examining the documents available to him to attain this goal: the latter may be classified in various categories.

The skilled man in the art is notably familiar with the processes for the manufacture of copolymers of acrylic acid with other water-soluble monomers using RAFT technology and particular transfer agents: xanthates. This method is designated in the literature by the term MADIX (Macromolecular Design via Interchange of Xanthates).

Thus, the document "Direct synthesis of double hydrophilic statistical di- and triblock copolymers comprised of acrylamide and acrylic acid units via the MADIX process" (Macromolecules Rapid Communications (2001), 22, 18, pages 1497-1503) teaches the synthesis of various copolymers of acrylic acid and of acrylamide by this means, using particular xanthates having the general formula $RS(C=S)OR'$.

In this publication, the synthesis of these xanthates is accomplished in the presence of pyridine, ethylene glycol and dichloromethane. Moreover, it appears that the various copolymers are manufactured in an essentially aqueous medium, but one which must necessarily contain isopropylic alcohol to dissolve the xanthates (see page 1498).

Similarly, document WO 98/58974 describes a process of the MADIX type for the synthesis of block polymers, from ethylenically unsaturated monomers, an initiator of radical polymerisation, and xanthates. Examples 1.1 to 1.12 demonstrate that the xanthates are always manufactured in the presence of organic solvents. It is thus possible to polymerise acrylic acid in a medium which may contain water, but necessarily another solvent such as acetone (examples 2.25 to 2.28).

One is also familiar with document WO 02/14535 which describes the synthesis of block copolymers of acrylic acid and acrylamide by the MADIX technique in a reactional medium containing water and a solvent such as isopropylic alcohol. The choice of solvent, as indicated on page 22, enables certain properties of the polymer, such as its molecular mass, to be regulated. In accordance with the MADIX techniques, the transfer agents are non-water-soluble xanthates.

With regard to the problem posed to the skilled man in the art, these processes are thus not satisfactory, since although it is possible to use water in the polymerisation medium, other organic solvents are still essential for it. In addition, the synthesis of the xanthates itself involves solvents other than water.

The skilled man in the art then turns to another group of processes of the RAFT type, in which the polymerisation of acrylic acid is accomplished in an exclusively aqueous medium.

Thus, document FR 2 821 620 describes a process of polymerisation of the RAFT type of acrylic acid and of its salts, in an aqueous or hydro-alcoholic system, leading to polymers of low polydispersity, using particular compounds of the type $RX(C=S)R'$ as transfer agents. It seems however on reading the examples that these agents are manufactured in the presence of a solvent which is eliminated by filtration and/or evaporation (example 1 tests 1 to 8).

Similarly, "Functional polymers from novel carboxy-terminated trithiocarbonates as highly efficient RAFT agents" (Polymer Preprints (2002), 43(2), 122-123) describes a process for synthesis of S,S' ($\alpha,\alpha'$ dimethylacetic acid) trithiocarbonate by reaction of $CS_2$ with hydroxide ions, followed by alkylation in the presence of chloroform and acetone. This product is used as a transfer agent to polymerise alkyl acrylates, acrylic acid and styrene, using a RAFT technique, in the presence of solvents such as butylicalcohol, acetone, an aromatic solvent and water in the precise case in which it is desired to polymerise acrylic acid.

The skilled man in the art is also familiar with document WO 03/66685. This introduces polymerisation by RAFT means with a high yield, a low polydispersity index, and the control of the structures obtained, of polymers and copolymers in a solvent. Water may be used as a solvent and acrylic acid is claimed in the list of polymerisable monomers. Nevertheless, synthesis of the transfer agent is complex. In addition, it uses solvents other than water and temperatures which are sometimes high (higher than 100° C.). As an illustration, example 11 describes the synthesis of naphtyl dithiocarbonylthio, which includes (among other stages) a stage of heating to 145° C. for 4 hours, a stage of dissolution in ethanol at 70° C., and a stage of purification in acetone and hexane.

Finally, the skilled man in the art is familiar with the document U.S. Pat. No. 6,596,899 which describes particular trithiocarbonates compounds (S,S' b ($\alpha,\alpha'$ disubstituate $\alpha''$ acetic acid) and its derivatives), enabling monomers such as acrylic acid to be polymerised by RAFT means. Polymerisation is undertaken in the possible presence of solvents such as $C_6$-$C_{12}$ alkanes, toluene, chlorobenzene, acetone, dimethylformamide, or water. These solvents are chosen so that they will not themselves act as transfer agents. Conversely, the synthesis of trithiocarbonate compounds is accomplished in the presence of organic solvents in which the reactive compounds are soluble.

Although they reveal the possibility of accomplishing polymerisations of acrylic acid by RAFT means in aqueous media, these documents do not constitute acceptable solutions to the problem posed to the skilled man in the art. Indeed, the transfer agents used must be systematically manufactured in the presence of organic solvents.

Finally, the skilled man in the art is familiar with the document FR 2 842 814. The latter describes a process for polymerisation of the RAFT type of acrylic acid in an aqueous solution, with a transfer agent which is a $\alpha$-substituent $\beta$-carboxylate xanthic salt synthesised in-situ in the aqueous solution. In his knowledge it is the only document in which the polymerisation of acrylic acid and the manufacture of the transfer agents do not use organic solvents. But this solution remains problematic. The xanthic salts give off a nauseous odour, which is found in the synthesised polymer. This odour constitutes a problem, both for the personnel involved in manufacturing the said polymers, and for the end user.

There is thus an evident requirement for the skilled man in the art to manufacture by RAFT means, without using organic solvents, and without using odorous xanthic salts, homopolymers of acrylic acid and copolymers of acrylic acid with other water-soluble monomers.

This need is reinforced by recent works which demonstrate, for the first time, that polyacrylic acid synthesised by the RAFT technique proves to be extremely effective as dispersing agent for mineral matter in water: "Synthesis and characterization of poly(acrylic acid) produced by RAFT polymerization: application as a very efficient dispersant of CaCO3, kaolin, and TiO2", (Macromolecules, 2003, 36, 3066). Indeed, this effectiveness in terms of dispersion was well known for polyacrylic acid as such, but had never been demonstrated in the case of a homopolymer obtained using the RAFT technique.

However, the only global teaching which this document indicates is that the reduction of the polydispersity index of the dispersing agent is a major factor in the dispersion of mineral fillers such as titanium dioxide, calcium carbonate or kaolin.

This document cites firstly complicated adsorption phenomena for calcium carbonate and kaolin (page 3076 lines 5-7), and secondly synthesis conditions which are unsatisfactory for the skilled man in the art: the polymerisation of acrylic acid is undertaken in the presence of methanol, ethanol, propanol-2 or dioxane, with all the problems of competition which may potentially exist between the solvent and the transfer agent.

At this stage, the Applicant continued with his research, and found in a surprising manner the solution to the problem of the manufacture of homopolymers of acrylic acid and copolymers of acrylic acid with other water-soluble monomers by RAFT means, without using organic solvents, without using odorous xanthic salts, and having carboxylic groups at the end of the chain in accordance with formula (III), refining a process for controlled radical polymerisation of the RAFT type, in water, which uses non-odorous transfer agents manufactured in water. This solution provides moreover polymers with a conversion rate higher than 90%, a polydispersity index lower than 2.2 and the possibility for the formulator to obtain the molecular weight of his choice.

At this stage, the Applicant is keen to indicate the techniques for measuring these various magnitudes, which will be the same throughout the remainder of the present application.

The conversion rate is measured by high performance liquid chromatography (HPLC). In this method, the components constituting the mixture are separated on a stationary phase and detected by a UV detector. After calibration of the detector, it is possible, starting from the area of the peak corresponding to the acrylic compound, to obtain the quantity of residual acrylic acid. This method forms part of the state of the art, and is described in many reference works such as, for example, in the manual "Experimental Organic Chemistry", by M. Chavanne, A. Julien, G. J. Beaudoin, E. Flamand, second Edition, Editions Modulo, chapter 18, pages 271-325.

The average molecular mass by weight and the polydispersity index are determined in aqueous media by a gel permeation chromatographic (GPC) method the standard for which is a series of 5 sodium polyacrylate standards supplied by Polymer Standard Service as references PAA 18K, PAA 8K, PAA 5K, PAA 4K and PAA 3K.

The Applicant stipulates in this respect that polyacrylate calibration is chosen since he feels that it is the most appropriate one for acrylic polymers, and since the results obtained depend on the type of calibration used, particularly for the polydispersity index.

The solution to the previously mentioned problem lies firstly in new compounds the chemical structure of which is in accordance with the following formula (I):

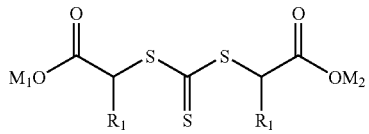

where $R_1$ designates an alkyl radical having 2 to 10 carbon atoms, an aromatic radical possibly substituted by an alkyl chain having 1 to 4 carbon atoms;

and where $M_1$ and $M_2$ designate the hydrogen atom, an amine salt, ammonium or an alkaline cation, and are identical or different.

The Applicant stresses that the document DD 217 214 reveals trithiocarbonate compounds of the type $S=C(SR)_2$, where R can be an alkyl grouping, which may possibly be carboxylated. However, this document in no way reveals the existence of particular compounds of formula (I) according to the invention.

The said compounds according to the invention are manufactured in water, according to the invention. They are then used as transfer agents for controlled radical polymerisation of the RAFT type, in water, of acrylic acid or of acrylic acid with water-soluble monomers.

The invention thus enables one to avoid the use of organic solvents, which are dangerous for human health and harmful for the environment, which can behave themselves as transfer agents, and lead to polymerisation by-products which are undesirable for end users, and which solvents must, finally, necessarily be eliminated, making the processes longer and more costly.

This method also allows one to avoid the use of xanthic salts, the unpleasant odour of which makes their use problematic.

In addition, homopolymers of acrylic acid and/or copolymers of acrylic acid with water-soluble monomers manufactured according to the invention have a polydispersity index lower than 2.2 and, finally, prove to be grinding and/or co-grinding aid agents, and very effective dispersion agents for aqueous suspensions of mineral matter.

The purpose of the invention is thus compounds the chemical structure of which is in accordance with the following formula (I):

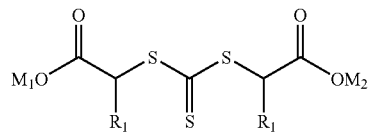

where $R_1$ designates an alkyl radical having 2 to 10 carbon atoms, an aromatic radical possibly substituted by an alkyl chain having 1 to 4 carbon atoms;

and where $M_1$ and $M_2$ designate the hydrogen atom, an amine salt, ammonium or an alkaline cation, and are identical or different.

Another object of the invention is a process for manufacturing in water the said compounds of formula (I), by:

a) Bringing into contact by pouring an aqueous solution of disodic trithiocarbonate $Na_2CS_3$ or an aqueous solution of dipotassic trithiocarbonate $K_2CS_3$ on a solution of a halogenated salt, which salt has a chemical structure in accordance with the following formula (II):

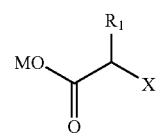

where $R_1$ designates an alkyl radical having 2 to 10 carbon atoms, an aromatic radical possibly substituted by an alkyl chain having 1 to 4 carbon atoms;

where M designates ammonium, or an alkaline cation such as sodium, potassium or lithium;

where X designates a halogen.

b) and possibly a stage of acidification of the compound after stage a).

Another object of the invention is the use as a transfer agent in a process of controlled radical polymerisation of the RAFT type, in water, of homopolymers of acrylic acid and/or copolymers of acrylic acid with other water-soluble monomers, of compounds having the following formula (I'):

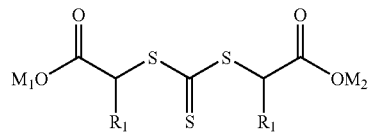

where $R_1$ designates an alkyl radical having 1 to 10 carbon atoms, an aromatic radical possibly substituted by an alkyl chain having 1 to 4 carbon atoms;

and where $M_1$ and $M_2$ designate the hydrogen atom, an amine salt, ammonium or an alkaline cation, and are identical or different.

Another object of the invention concerns the homopolymers of acrylic acid and/or copolymers of acrylic acid with other water-soluble monomers, obtained according to the invention and having a polydispersity index lower than 2.2, whilst containing at the end of the chain a pattern in accordance with the following formula (III):

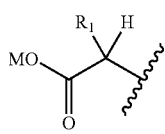

where $R_1$ designates an alkyl radical having 1 to 10 carbon atoms, an aromatic radical possibly substituted by an alkyl chain having 1 to 4 carbon atoms;

and where M designates the hydrogen atom, an amine salt, ammonium or an alkaline cation, and are identical or different.

Another object of the invention is the use of the said homopolymers of acrylic acid and/or of the said copolymers of acrylic acid with other water-soluble monomers, as grinding aid and/or co-grinding aid agents of mineral matter in water.

Another object of the invention is the use of the said homopolymers of acrylic acid and/or of the said copolymers of acrylic acid with other water-soluble monomers, as agents for dispersion of mineral matter in water. The Applicant stipulates at this point that all dispersing agents well known by the skilled man in the art are not necessarily grinding aid agents.

Another object of the invention concerns the said aqueous dispersions and suspensions of mineral matter.

Another object of the invention is the use of the said dispersions and suspensions of mineral matter in paper formulations, and notably in coating colours and mass fillings, in paint, plastic, cement and ceramic formulations, in formulations for the treatment of water, in detergent and cosmetic formulations, and in drilling muds.

Another object of the invention is the direct use, as a dispersing agent, of homopolymers of acrylic acid and/or of copolymers of acrylic acid with other water-soluble monomers according to the invention, in paper formulations, and notably in coating colours and mass fillings, in paint, cement and ceramic formulations, in formulations for the treatment of water, in detergent, cosmetic and ceramic formulations, and in drilling muds.

Another object of the invention concerns paper formulations, and notably coating colours and mass fillings, paint, plastic, cement and ceramic formulations, formulations for the treatment of water, detergent and cosmetic formulations, and drilling muds, obtained through the use in the said formulations of the aqueous dispersions and suspensions of mineral matter according to the invention.

A final object of the invention concerns paper formulations, and notably coating colours and mass fillings, paint, plastic, cement and ceramic formulations, formulations for the treatment of water, detergent and cosmetic formulations, and drilling muds, obtained by direct use as a dispersing agent in the said formulations of the polymers according to the invention.

The new compounds according to the invention are manufactured in water. When used as transfer agents in a polymerisation process of the RAFT type, in water, they enable homopolymers of acrylic acid and/or copolymers of acrylic acid to be manufactured with other water-soluble monomers.

By this means the use of organic solvents is avoided, both during the manufacture of the transfer agents, and also during the polymerisation stage. These solvents are dangerous for human health, and harmful for the environment. They can themselves behave as transfer agents and lead to polymerisation by-products which are undesirable for the end user.

Finally, these solvents must necessarily be eliminated, making the processes longer, more costly and more dangerous.

This method also allows one to avoid the use of odorous xanthic salts, the unpleasant odour of which makes their use problematic.

Finally, polymers with a polydispersity index lower than 2.2 are obtained, which prove to be grinding and/or co-grinding aid agents, and dispersion agents which are very effective for aqueous suspensions of mineral matter.

These aims are attained through the use of compounds the chemical structure of which is in accordance with the following formula (I):

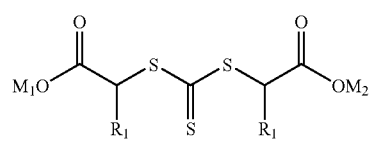

where $R_1$ designates an alkyl radical having 2 to 10 carbon atoms, an aromatic radical possibly substituted by an alkyl chain having 1 to 4 carbon atoms;

and where $M_1$ and $M_2$ designate the hydrogen atom, an amine salt, ammonium or an alkaline cation, and are identical or different.

The amines are chosen from among the aliphatic and/or cyclic primary, secondary or tertiary amines such as, for example, stearylamine, the ethanolamines (mono-, di-, triethanolamine), mono and diethylamine, cyclohexylamine, methylcyclohexylamine, amino methyl propanol and morpholine.

The alkaline cations are chosen from among sodium, potassium and lithium.

Preferentially, $R_1$ is an alkyl radical having 2 to 6 carbon atoms, and $M_1$ and $M_2$ are identical and designate the hydrogen atom, sodium or potassium.

In a more preferential manner, $R_1$ is an alkyl radical having 2 to 6 carbon atoms, and $M_1$ and $M_2$ are identical and designate the hydrogen atom or sodium.

In an even more preferential manner, RI is an alkyl radical having 2 to 4 carbon atoms, and $M_1$ and $M_2$ are identical and designate the hydrogen atom or sodium.

In a yet more preferential manner, $R_1$ is the alkyl radical having 4 carbon atoms, and $M_1$ and $M_2$ are identical and designate the hydrogen atom or sodium.

In a yet more preferential manner, $R_1$ is the alkyl radical having 4 carbon atoms, and $M_1$ and $M_2$ are identical and designate sodium.

Another object of the invention is a process for manufacturing in water the said compounds of formula (I), by:

a) Bringing into contact by pouring an aqueous solution of disodic trithiocarbonate $Na_2CS_3$ or an aqueous solution of dipotassic trithiocarbonate $K_2CS_3$ on a solution of a halogenated salt, which salt has a chemical structure in accordance with the following formula (II):

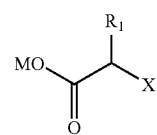

where $R_1$ designates an alkyl radical having 2 to 10 carbon atoms, an aromatic radical possibly substituted by an alkyl chain having 1 to 4 carbon atoms;

where M designates ammonium, or an alkaline cation such as sodium, potassium or lithium;

where X designates a halogen.

b) and possibly a stage of acidification of the compound after stage a).

The alkaline cations are chosen from among sodium, potassium and lithium.

Preferentially, $R_1$ is an alkyl radical having 2 to 6 carbon atoms, and M designates sodium or potassium.

In a more preferential manner, $R_1$ is an alkyl radical having 2 to 4 carbon atoms, and M designates sodium or potassium.

In a yet more preferential manner, $R_1$ is the alkyl radical having 4 carbon atoms, and M designates sodium.

Preferentially, X designates bromine.

Another object of the invention is the use as transfer agents in a process of controlled radical polymerisation of the RAFT type, in water, of homopolymers of acrylic acid and/or copolymers of acrylic acid with other water-soluble monomers, of compounds characterised in that they have a chemical structure in accordance with the following formula (I'):

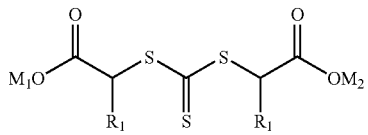

where $R_1$ designates an alkyl radical having 1 to 10 carbon atoms, an aromatic radical possibly substituted by an alkyl chain having 1 to 4 carbon atoms;

and where $M_1$ and $M_2$ designate the hydrogen atom, an amine salt, ammonium or an alkaline cation, and are identical or different.

The amines are chosen from among the aliphatic and/or cyclic primary, secondary or tertiary amines such as, for example, stearylamine, the ethanolamines (mono-, di-, triethanolamine), mono and diethylamine, cyclohexylamine, methylcyclohexylamine, amino methyl propanol and morpholine.

The alkaline cations are chosen from among sodium, potassium and lithium.

Preferentially, $R_1$ is an alkyl radical having 2 to 6 carbon atoms, and $M_1$ and $M_2$ are identical and designate the hydrogen atom, sodium or potassium.

In a more preferential manner, $R_1$ is an alkyl radical having 2 to 6 carbon atoms, and $M_1$ and $M_2$ are identical and designate the hydrogen atom or sodium.

In an even more preferential manner, $R_1$ is an alkyl radical having 2 to 4 carbon atoms, and $M_1$ and $M_2$ are identical and designate the hydrogen atom or sodium.

In a yet more preferential manner, $R_1$ is the alkyl radical having 4 carbon atoms, and $M_1$ and $M_2$ are identical and designate the hydrogen atom or sodium.

In a yet more preferential manner, $R_1$ is the alkyl radical having 4 carbon atoms, and $M_1$ and $M_2$ are identical and designate sodium.

This use of compounds according to the invention as transfer agents in a process for controlled radical polymerisation of the RAFT type, in water, of homopolymers of acrylic acid and/or copolymers of acrylic acid with other water-soluble monomers, is also characterised in that the said process is undertaken continuously, in a batch or semi-batch manner. By a batch process, the Applicant means a polymerisation process in which all the monomers are introduced in the initial stage. By a semi-batch process, the Applicant means a polymerisation process in which all the monomers are introduced throughout the polymerisation.

Preferentially, this use is characterised in that said process is realised in batch or in semi-batch.

Another object of the invention concerns the homopolymers of acrylic acid and/or copolymers of acrylic acid obtained by the controlled radical polymerisation process of the RAFT type, in water, according to the invention, and characterised in that they have a polydispersity index lower than 2.2, and contain at the end of the chain a pattern in accordance with the following formula (III):

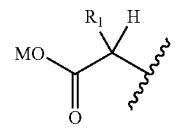

where $R_1$ designates an alkyl radical having 1 to 10 carbon atoms, an aromatic radical possibly substituted by an alkyl chain having 1 to 4 carbon atoms;

and where M designates the hydrogen atom, an amine salt, ammonium or an alkaline cation.

The amines are chosen from among the aliphatic and/or cyclic primary, secondary or tertiary amines such as, for example, stearylamine, the ethanolamines (mono-, di-, triethanolamine), mono and diethylamine, cyclohexylamine, methylcyclohexylamine, amino methyl propanol and morpholine.

The alkaline cations are chosen from among sodium, potassium and lithium.

Preferentially, $R_1$ is an alkyl radical having 2 to 6 carbon atoms, and M designates the hydrogen atom, sodium or potassium.

In a more preferential manner, $R_1$ is an alkyl radical having 2 to 6 carbon atoms, and M designates the hydrogen atom or sodium.

In a yet more preferential manner, $R_1$ is an alkyl radical having 2 to 4 carbon atoms, and M designates the hydrogen atom or sodium.

In a yet more preferential manner, $R_1$ is the alkyl radical having 4 carbon atoms, and M designates the hydrogen atom or sodium.

In a yet more preferential manner, $R_1$ is the alkyl radical having 4 carbon atoms, and M designates sodium.

The copolymers of acrylic acid with other water-soluble monomers according to the invention are also characterised in that the water-soluble monomers are chosen from among methacrylic acid, itaconic acid, maleic acid, 2-acrylamido-2-methyl-1-propane sulphonic acid in acid form or partially neutralised, 2-methacrylamido-2-methyl-1-propane sulphonic acid in acid form or partially neutralised, 3-methacrylamido-2-hydroxy-1-propane sulphonic acid in acid form or partially neutralised, allylsulphonic acid, methallylsulphonic acid, allyloxybenzene sulphonic acid, methallyloxybenzene sulphonic acid, 2-hydroxy-3-(2-propenyloxy)propane sulphonic acid, 2-methyl-2-propene-1-sulphonic acid, ethylene sulphonic acid, propene sulphonic acid, styrene sulphonic acid, together with all their salts, vinyl sulphonic acid, sodium methallylsulfonate, sulfopropyl acrylate or methacrylate, sulfomethylacrylamide, sulfomethylmethacrylamide or from among acrylamide, methylacrylamide, n-methylolacrylamide, n-acryloylmorpholine, ethylene glycol methacrylate, ethylene glycol acrylate, propylene glycol methacrylate, propylene glycol acrylate, methoxy polyethylene glycol acrylate, methoxy polyethylene glycol methacrylate, propene phosphonic acid, acrylate phosphate or ethylene methacrylate or propylene glycol or from among vinylpyrrolidone, methacrylamido propyl trimethyl ammonium chloride or sulphate, trimethyl ammonium ethyl chloride or sulphate methacrylate, together with their acrylate and acrylamide counterparts, whether quaternised or not, and/or ammonium dimethyldiallylchloride, and mixtures thereof.

Homopolymers of acrylic acid and/or copolymers of acrylic acid with other water-soluble monomers obtained according to the invention, are also characterised in that they have an average molecular mass by weight ($M_w$) of between 1000 g/mole and 100,000 g/mole, preferentially between 1000 g/mole and 50,000 g/mole, very preferentially between 1000 g/mole and 30,000 g/mole, and extremely preferentially between 1000 g/mole and 20,000 g/mole, according to the method described above.

Homopolymers of acrylic acid and/or copolymers of acrylic acid with other water-soluble monomers obtained according to the invention are also characterised in that they have a conversion rate higher than 90%, preferentially higher than 95%, and very preferentially higher than 99%.

These homopolymers and/or these copolymers according to the invention are either in their acid form, i.e. non-neutralised, or partially or totally neutralised by one or more monovalent, divalent or trivalent neutralisation agents, or neutralisation agents with higher valency, or mixtures thereof.

The monovalent neutralisation agents are chosen from the group constituted by the compounds containing alkaline cations, particularly sodium and potassium, or again lithium, ammonium, or again the aliphatic and/or cyclic primary or secondary amines such as, for example, the ethanolamines, mono- and diethylamine, or cyclohexylamine.

The divalent or trivalent neutralisation agents, or neutralisation agents with higher valency, are chosen from the group constituted by the compounds containing divalent cations belonging to the alkaline earths, particularly magnesium and calcium, or again zinc, and also from the trivalent cations, particularly aluminium, or again from certain compounds containing cations with a higher valency.

Another object of the invention is the use as grinding aid and/or co-grinding aid agent of mineral matter in water, of the homopolymers of acrylic acid and/or copolymers of acrylic acid, according to the invention.

The Applicant stipulates that the operation to grind the mineral substance to be refined consists in grinding the mineral substance with a grinding body into very fine particles in an aqueous medium containing the grinding aid agent. In a different manner, the dispersion operation consists in suspending the mineral matter in water, in the presence of a dispersing agent, to obtain by this means a suspension which is stable over time, without reducing the particles' size.

In addition, the Applicant stipulates that the co-grinding operation consists in grinding a mixture of at least 2 mineral fillers.

Thus, the grinding body, of granulometry advantageously of between 0.20 and 4 millimeters, is added to the aqueous suspension of the mineral substance for grinding. The grinding body generally has the form of particles of materials as diverse as silicon dioxide, aluminium oxide, zirconium oxide or mixtures thereof, together with synthetic resins of great hardness, steels or other. An example of the composition of such grinding bodies is given by patent FR 2 303 681 which describes the grinding elements formed 30% to 70% by weight of zirconium oxide, 0.1% to 5% of aluminium oxide, and 5 to 20% of silicon dioxide.

The grinding body is preferably added to the suspension in a quantity such that the ratio by weight between this grinding material and the mineral substance for grinding is at least 2/1, this ratio being preferably between the limits 3/1 and 5/1.

The mixture of the suspension and of the grinding body is then subjected to the mechanical stirring action, as this occurs in a traditional grinder with micro-elements.

The time required to attain the desired refinement of the mineral substance after grinding will be defined by the skilled man in the art according to the nature and quantity of the mineral substances to be ground, and according to the stirring method used and the temperature of the medium during the grinding operation.

The use as grinding aid and/or co-grinding aid agent of mineral matter in water, of the polymers according to the invention is also characterised in that the mineral matter is chosen from among natural or synthetic calcium carbonate, the dolomites, kaolin, talc, gypsum, titanium oxide, satin white or aluminium trihydroxide, mica and mixtures thereof of at least two of these fillers, such as talc-calcium carbonate mixtures, calcium carbonate-kaolin mixtures or mixtures of calcium carbonate with aluminium trihydroxide, or again mixtures with synthetic or natural fibres or again mineral co-structures such as talc-calcium carbonate or talc-titanium dioxide co-structures. These mineral matters are preferentially a calcium carbonate chosen from among marble, calcite, chalk, or mixtures thereof.

The use as grinding aid and/or co-grinding aid agent of mineral matter in water of the polymers according to the invention is also characterised in that 0.05% to 5% by dry weight of the polymers according to the invention is used, relative to the dry weight of the mineral matter, and again more particularly 0.1% to 3% by dry weight of the polymers according to the invention, relative to the dry weight of mineral matter.

Another object of the invention is the use as dispersing agents of mineral matter in water of the homopolymers of acrylic acid and/or of the copolymers of acrylic acid with water-soluble monomers, according to the invention.

The use as dispersing agents of mineral matter in water of the polymers according to the invention is also characterised in that the mineral matter is chosen from among natural or synthetic calcium carbonate, the dolomites, kaolin, talc, gypsum, satin white or aluminium trihydroxide, mica and mixtures thereof of at least two of these fillers, such as talc-calcium carbonate mixtures, calcium carbonate-kaolin mixtures or mixtures of calcium carbonate with aluminium trihydroxide, or again mixtures with synthetic or natural fibres or again mineral co-structures such as talc-calcium carbonate or talc-titanium dioxide co-structures.

This mineral matter is preferentially a calcium carbonate chosen from among marble, calcite, chalk, or mixtures thereof.

The use as dispersing agents of mineral matter in water of the polymers according to the invention is also characterised in that 0.05% to 5% by dry weight of the polymers according to the invention is used, relative to the dry weight of the mineral matter, and again more particularly 0.1% to 3% by dry weight of the polymers according to the invention, relative to the dry weight of mineral matter.

Another object of the invention concerns aqueous suspensions and dispersions of mineral matter obtained by use of the polymers according to the invention.

Aqueous suspensions of mineral matter according to the invention are characterised in that the mineral matter is chosen from among natural or synthetic calcium carbonate, the dolomites, kaolin, talc, gypsum, titanium oxide, satin white or aluminium trihydroxide, mica and mixtures thereof of at least two of these fillers, such as talc-calcium carbonate mixtures, calcium carbonate-kaolin mixtures or mixtures of calcium carbonate with aluminium trihydroxide, or again mixtures with synthetic or natural fibres or again mineral co-structures such as talc-calcium carbonate or talc-titanium dioxide co-structures. This mineral matter is preferentially a calcium carbonate chosen from among marble, calcite, chalk, or mixtures thereof.

Aqueous dispersions of mineral matter according to the invention are characterised in that the mineral matter is chosen from among natural or synthetic calcium carbonate, the dolomites, kaolin, talc, gypsum, satin white or again aluminium trihydroxide, mica and mixtures thereof of at least two of these fillers, such as talc-calcium carbonate mixtures, calcium carbonate-kaolin mixtures or mixtures of calcium carbonate with aluminium trihydroxide, or again mixtures with synthetic or natural fibres or again mineral co-structures such as talc-calcium carbonate or talc-titanium dioxide co-structures. This mineral matter is preferentially a calcium carbonate chosen from among marble, calcite, chalk, or mixtures thereof.

The aqueous suspensions and dispersions of mineral matter according to the invention are characterised in that they contain 0.05% to 5% by dry weight of the polymers according to the invention relative to the dry weight of mineral matter, and again more particularly 0.1% to 3% by dry weight of the polymers according to the invention, relative to the dry weight of mineral matter.

Another object of the invention is the use of the aqueous dispersions and suspensions of mineral matter according to the invention in paper formulations, and notably in coating colours and mass fillings, in paint, plastic, cement and ceramic formulations, in formulations for the treatment of water, in detergent and cosmetic formulations, and in drilling muds.

Another object of the invention is the direct use as dispersing agents in paper formulations, and notably in coating colours and mass fillings, in paint, ceramic and cement formulations, in formulations for the treatment of water, in detergent and cosmetic formulations, and in drilling muds, of the polymers obtained according to the invention.

This direct use in paper formulations, and notably in coating colours and mass fillings, in paint, plastic and cement formulations, in formulations for the treatment of water, in detergent and cosmetic formulations and in drilling muds, of the polymers according to the invention, is also characterised in that 0.05% to 3% by dry weight of the polymers according to the invention is used, relative to the dry weight of mineral matter, and again more particularly 0.1% to 3% by dry weight of the polymers according to the invention, relative to the dry weight of mineral matter.

A final object of the invention concerns paper formulations, and notably coating colours and mass fillings, paint, plastic, ceramic and cement formulations, formulations for the treatment of water, detergent and cosmetic formulations, and drilling muds, obtained according to the invention.

The scope and interest of the invention will be better appreciated through the following examples, which are by no means limitative.

EXAMPLE 1

The purpose of this example is to present the synthesis of new compounds according to the invention, the chemical structure of which is in accordance with formula (I).
Test n° 1
Preparation of compound A of formula (I):

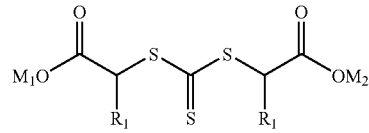

where $R_1$ designates the alkyl radical having 4 carbon atoms;
and $M_1$ and $M_2$ designate the sodium atom Na.
In a beaker under magnetic stirring, the following are weighed:
30 grams of water;
19.5 grams of 2 bromohexanoic acid.
The mixture is neutralised with a 50% soda solution until a pH equal to 6.5 is obtained. The temperature increases to 52° C. A homogeneous solution is then obtained which is cooled to 43° C.
30.8 grams of an aqueous solution equal to 25% disodic trithiocarbonate solution is then poured drop by drop during a 20-minute period.
It is left to react for 2 hours, under stirring action. The alkylation S reaction is slightly exothermic and the temperature increases to 47° C., while the pH settles at 10.
A clear yellow solution is obtained containing compound A.

EXAMPLE 2

The purpose of this example is to illustrate the use according to the invention of sulphurous compounds in a controlled radical polymerisation process of the RAFT type, in water, of homopolymers of acrylic acid according to the invention.
Test n° 2
In a 1-liter reactor fitted with a mechanical stirrer and heating of the oil bath type, the following is introduced:
150 grams of water;
50 grams of acrylic acid;
17.1 grams of a 17.1% solution containing the compound of formula (I'):

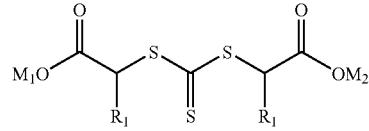

where $R_1$ designates the alkyl radical having 1 carbon atom;
and $M_1$ and $M_2$ designate the sodium atom Na.
0.4 g of a polymerisation initiator 4,4' azobis(4-cyanopentanoic) sold by the company Aldrich under the name V501.
Under stirring, the mixture is heated to a temperature equal to 100° C. The temperature is then maintained at 95° C. for 2 hours. A clear, slightly orangey solution is then obtained, which is cooled to ambient temperature.

This solution is neutralised with soda until a pH equal to 8.5 is obtained; a solution is then obtained which contains a homopolymer of acrylic acid neutralised by sodium.

Test n° 3

In a 1-liter reactor fitted with a mechanical stirrer and heating of the oil bath type, the following is introduced:
- 300 grams of water;
- 100 grams of acrylic acid;
- 34 grams of a solution containing the compound of formula (I'):

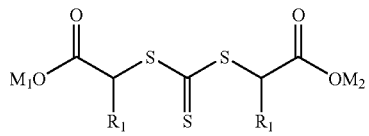

where $R_1$ designates the alkyl radical having 1 carbon atom;

and $M_1$ and $M_2$ designate the sodium atom Na.

- 0.8 grams of a polymerisation initiator 4,4' azobis(4-cyanopentanoic) sold by the company Aldrich under the name V501.

Under stirring, the mixture is heated to a temperature equal to 100° C. The temperature is then maintained at 95° C. for 2 hours.

A clear, slightly orangey solution is then obtained, which is cooled to ambient temperature.

This solution is neutralised with a molar mixture of 30% lime and 70% soda until a pH equal to 8.5 is obtained; a solution is then obtained which contains a homopolymer of acrylic acid neutralised 30% by calcium and 70% by sodium.

Test n° 4

In a 1-liter reactor fitted with a mechanical stirrer and heating of the oil bath type, the following is introduced:
- 150 grams of water;
- 50 grams of acrylic acid;
- 17.07 grams of the test solution n° 1 containing compound A;
- 0.4 grams of a polymerisation initiator 4,4' azobis(4-cyanopentanoic) sold by the company Aldrich under the name V501.

Under stirring, the mixture is heated to a temperature equal to 100° C.

The temperature is then maintained at 95° C. for 2 hours. A clear, slightly orangey solution is then obtained, which is cooled to ambient temperature.

This solution is neutralised with a molar mixture of 30% lime and 70% soda until a pH equal to 8.5 is obtained; a solution is then obtained which contains a homopolymer of acrylic acid neutralised 30% by calcium and 70% by sodium.

Test n° 5

In a 1-liter reactor fitted with a mechanical stirrer and heating of the oil bath type, the following is introduced:
- 300 grams of water;
- 100 grams of acrylic acid;
- 23.9 grams of the test solution n° 1 containing compound A;
- 0.56 grams of a polymerisation initiator 4,4' azobis(4-cyanopentanoic) sold by the company Aldrich under the name V501.

Under stirring, the mixture is heated to a temperature equal to 100° C. The temperature is then maintained at 95° C. for 2 hours. A clear, slightly orangey solution is then obtained, which is cooled to ambient temperature.

This solution is neutralised with soda until a pH equal to 8.5 is obtained; a solution is then obtained which contains a homopolymer of acrylic acid neutralised by sodium.

Test n° 6

In a 1-liter reactor fitted with a mechanical stirrer and heating of the oil bath type, the following is introduced:
- 300 grams of water;
- 100 grams of acrylic acid;
- 16.8 grams of the solution of test n° 1;
- 1.04 grams of a polymerisation initiator 4,4' azobis(4-cyanopentanoic) sold by the company Aldrich under the name V501.

Under stirring, the mixture is heated to a temperature equal to 100° C. The temperature is then maintained at 95° C. for 2 hours. A clear, slightly orangey solution is then obtained, which is cooled to ambient temperature.

This solution is neutralised with soda until a pH equal to 8.5 is obtained; a solution is then obtained which contains a homopolymer of acrylic acid neutralised by sodium.

Test n° 7

In a 1-liter reactor fitted with a mechanical stirrer and heating of the oil bath type, the following is introduced:
- 300 grams of water;
- 100 grams of acrylic acid;
- 18.6 grams of the test solution n° 1 containing compound A;
- 0.44 grams of a polymerisation initiator 4,4' azobis(4-cyanopentanoic) sold by the company Aldrich under the name V501.

Under stirring, the mixture is heated to a temperature equal to 100° C. The temperature is then maintained at 95° C. for 2 hours.

A clear, slightly orangey solution is then obtained, which is cooled to ambient temperature.

This solution is neutralised with soda until a pH equal to 8.5 is obtained; a solution is then obtained which contains a homopolymer of acrylic acid neutralised by sodium.

For all the tests n° 2 to 7, the rate of conversion of the polymer by HPLC, its molecular mass by weight ($M_w$) and its polydispersity index are obtained by GPC, together with the presence of the pattern of formula (III) at the end of the polymer chain using the methods which have been previously set out, and through the use for the HPLC analysis of an HPLC set of Philips brand of reference PU 4100 with a UV/visible detector of reference PU 4110, for the GPC analysis of a GPC machine of Waters brand, consisting of a Waters 515 pump, of one or two Ultrahydrogel linear columns of dimensions 7.8 mm×30 cm (pore diameter 120 to 2000 Å) with a guard column and a Waters refractometer of reference 410, and finally, for the MALDI TOF analysis, a time of flight machine called Voyager-DE STR from PerSeptive Biosystems, using a nitrogen laser (337 nm) and an acceleration voltage of 20 kV.

The corresponding results are grouped together in table 1.

TABLE 1 characteristics of the homopolymers of acrylic acid obtained according to the invention with:

| Test n° | Neut. Sys. | $M_w$ | $I_p$ | $T_c$ (%) |
|---|---|---|---|---|
| 2 | Na | 6800 | 1.60 | 99.1 |
| 3 | 30% Ca 70% Na | 6300 | 1.55 | 99.2 |
| 4 | 30% Ca 70% Na | 6700 | 1.72 | 99.8 |

TABLE 1-continued characteristics of the homopolymers of acrylic acid obtained according to the invention with:

| Test n° | Neut. Sys. | $M_w$ | $I_p$ | $T_c$ (%) |
|---|---|---|---|---|
| 5 | Na | 8000 | 2.10 | 99.6 |
| 6 | Na | 11800 | 1.95 | 98.9 |
| 7 | Na | 9600 | 2.04 | 99.0 |

Neut. Sys.: nature of the neutralisation system
$M_w$: molecular mass by weight (g/mole)
$I_p$: polydispersity index
$T_c$: conversion rate (%)

Tests n° 2 to 7 demonstrate that it was possible to obtain, using a polymerisation process according to the invention, homopolymers of acrylic acid having a polydispersity index lower than 2.2, an average molecular mass by weight of between 6 000 g/mole and 20 000 g/mole, and a conversion rate higher than 98%, and having a pattern of formula (III) at the end of the chain.

EXAMPLE 3

This example illustrates the use of a polymer obtained according to the invention as a grinding aid agent of mineral matter and more specifically calcium carbonate. This example also illustrates the process of obtaining aqueous suspensions of calcium carbonate according to the invention.

It should also be noted that these suspensions of calcium carbonate according to the invention are refined, highly concentrated with mineral matter and easily handled by the end user, i.e. easily used both for coating of paper and for mass-filling of paper.

To do so, an aqueous suspension is prepared from calcium carbonate from the Orgon deposit (France), of median diameter of around 7 micrometers.

The aqueous suspension has a dry matter concentration of 76% by weight relative to the total mass.

The grinding aid agent is introduced into this suspension according to the quantities indicated in the table below, expressed as a percentage of dry weight relative to the dry calcium carbonate mass to be ground.

The suspension circulates in a grinder of the Dyno-Mill™ type with a fixed cylinder and rotating pulser, the grinding body of which is constituted by corundum balls of diameter in the range 0.6 millimeter to 1.0 millimeter.

The total volume occupied by the grinding body is 1,150 cubic centimeters, while its mass is 2,900 g.

The grinding chamber has a volume equal to 1,400 cubic centimeters.

The circumferential speed of the grinder is 10 meters per second.

The calcium carbonate suspension is recycled at a rate of 18 liters per hour.

The outlet of the Dyno-Mill™ is fitted with a 200 micron mesh separator enabling the suspension resulting from the grinding and the grinding body to be separated.

The temperature during each grinding test is maintained at 60° C. approximately.

On completion of the grinding ($T_o$), a sample of the pigment suspension is recovered in a flask.

The granulometry of the suspensions is determined using a Sédigraph™ 5100 granulometer from the company Micromeritics. The demand for dispersant is then calculated: it is defined as the % by weight of dry polymer used, relative to the dry weight of mineral fillers, to obtain a given granulometry. For all tests 8 to 11, this granulometry is determined such that 80% of the particles have an average diameter lower than 1 μm.

The Brookfield™ viscosity of the suspension is measured using a Brookfield™ viscometer type RVT, at a temperature of 25° C. and rotational speeds of 10 revolutions per minute and 100 revolutions per minute with the adequate mobile. The viscosity is read after one minute of rotation. An initial viscosity is thus obtained at T=0. After a settlement time of 8 days, the viscosity is measured again: this is the viscosity at T=8 days before stirring. The same viscosity measurement is undertaken after having stirred the suspension for 5 minutes. This is the viscosity at T=8 days after stirring.

Test n° 8

This test illustrates the prior art and uses 1.06% by dry weight, relative to the dry weight of calcium carbonate, of a polyacrylate, obtained by a traditional process of radical polymerisation, of molecular weight by weight equal to 5,600 g/mole, of polydispersity index equal to 2.4 (as determined by the methods described above) and neutralised by a calcium-sodium mixture in a molar ratio equal to 30/70.

Test n° 9

This test illustrates the prior art and uses 1.04% by dry weight, relative to the dry weight of calcium carbonate, of a polyacrylate, obtained by a process of radical polymerisation of the RAFT type, using dibenzyl trithiocarbonate as the transfer agent, and polymerised in ethanol using the method described in the French patent application FR 2 821 620. This is a polyacrylate of molecular weight equal to 5,955 g/mole, of polydispersity index equal to 1.95 (as determined by the methods described above) and neutralised by calcium-sodium mixture in a molar ratio equal to 30/70.

Test n° 10

This test illustrates the prior art and uses 1.00% by dry weight, relative to the dry weight of calcium carbonate, of a polyacrylate, obtained by a process of controlled radical polymerisation in water, using a carboxylate xanthate having the following formula:

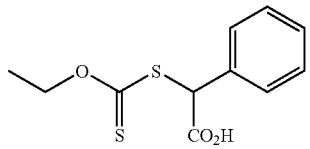

The manufactured polymer is a polyacrylate of molecular weight equal to 7,725 g/mole, of polydispersity index equal to 2.00 (as determined by the methods described above) and neutralised by a calcium-sodium mixture in a molar ratio equal to 30/70.

Test n° 11

This test illustrates the invention and uses the polyacrylate according to the invention of test n° 4.

Test n° 12

This test illustrates the invention and uses the polyacrylate according to the invention of example n° 3.

The characteristics of the polymers used (molecular weight, polydispersity index, conversion rate), the corresponding demand for polymer, together with the various measured Brookfield™ viscosities, are recorded in table 2.

TABLE 2 use as grinding aid agents of polyacrylates of the prior art and of polyacrylates according to the invention.

| n° test | Prior Art./ Inv. | Polymer Ip | Mw | Tc | % in disp. | T = 0 10 rpm | 100 rpm | Brookfield™ viscosity (mPa·s) 8 days AVAG 10 rpm | 100 rpm | 8 days APAG 10 rpm | 100 rpm |
|---|---|---|---|---|---|---|---|---|---|---|---|
| 8 | Prior art | 2.4 | 5600 | >99 | 1.07 | 2170 | 668 | 9413 | 1705 | 2423 | 794 |
| 9 | Prior art | 1.95 | 5955 | 99.5 | 1.04 | 1724 | 498 | 3610 | 935 | 1454 | 464 |
| 10 | Prior art | 2.00 | 7725 | 99 | 1.00 | 1693 | 522 | 6439 | 1384 | 1678 | 533 |
| 11 | Inv. | 1.72 | 6700 | 99.8 | 0.96 | 1313 | 376 | 2196 | 648 | 1290 | 395 |
| 12 | Inv. | 1.55 | 6300 | 99.2 | 0.99 | 951 | 308 | 1475 | 521 | 729 | 253 |

$I_p$: polydispersity index
$M_w$: molecular weight (g/mole)
$T_c$: conversion rate (%)
% in disp.: demand for dispersant (% by dry polymer weight/dry weight of fillers)

The results of table 2 show that the polymers according to the invention have polydispersity indices well below 2.2 and lower in all cases than those of the polymers of the prior art. Similarly, the conversion rates of the polymers according to the invention are without exception higher than those of the polymers of the prior art.

It is thus demonstrated that the polymers manufactured according to the invention are more monodisperse than those of the prior art.

In addition, the demand for polymer according to the invention is still lower than the demand for polymer of the prior art: this represents a net advantage for the end user.

Finally, the suspensions of mineral fillers manufactured with the polymers according to the invention are more stable over time than those obtained from the polymers of the prior art: the polymers according to the invention are thus more effective than those of the prior art.

EXAMPLE 4

The purpose of this example is to illustrate the use according to the invention of a sulphurous compound according to the invention, in a process for controlled radical polymerisation of the RAFT type, in water, and in semi-batch mode, of homopolymers of acrylic acid according to the invention.

For tests n° 13 to n° 21, one starts by introducing, into a 2-liter reactor fitted with a mechanical stirrer and heating of the oil bath type, water and an aqueous solution containing the sulphurous transfer agent which is compound A obtained in test n° 1.

Whilst stirring, the bath holder bottom is then heated to a temperature equal to 95° C. Keeping this temperature constant at ±2° C., one adds, during a period of 1 hour and using peristaltic pumps, the acrylic acid and the catalysts (sodium persulphate and metabisulphite, respectively $Na_2S_2O_8$ and $Na_2S_2O_5$). The temperature is then kept constant at 95° C.±2° C. for 2 hours.

The solution obtained is neutralised with soda until pH=8.5. One then obtains a clear, slightly orangey solution, which is cooled to ambient temperature and which contains a homopolymer of acrylic acid according to the invention, neutralised by sodium.

Table 3 indicates the quantity (in grams) of the various products used, together with the molecular weight $M_w$ (in g/mole), the polydispersity index $I_p$ and the conversion rate $T_c$, measured for the polymers obtained, which parameters are determined according to the methods described above in the present application.

TABLE 3 homopolymers of acrylic acid according to the invention

| Test n° | Water | Acrylic acid | Transfer agent according to the invention* | Catalysts $Na_2S_2O_8$ | $Na_2S_2O_5$ | Properties of the homopolymers according to the invention $M_w$ | $I_p$ | $T_c$ |
|---|---|---|---|---|---|---|---|---|
| 13 | 400 | 400 | 180 | 4.68 | 1.336 | 4640 | 1.83 | >99 |
| 14 | 400 | 400 | 138.4 | 3.51 | 1.002 | 6550 | 1.80 | >99 |
| 15 | 400 | 400 | 138.4 | 5.85 | 1.67 | 7075 | 1.87 | >99 |
| 16 | 400 | 400 | 108 | 4.68 | 1.336 | 8420 | 2.10 | >99 |
| 17 | 400 | 400 | 90 | 2.34 | 0.668 | 10235 | 1.90 | >99 |
| 18 | 400 | 400 | 90 | 4.68 | 1.336 | 10940 | 1.80 | >99 |
| 19 | 400 | 400 | 77.5 | 3.51 | 1.002 | 12600 | 2.08 | >99 |

TABLE 3-continued homopolymers of acrylic acid according to the invention

| | | Constituents (masses in grams) | | | | Properties of the homopolymers according to the invention | | |
|---|---|---|---|---|---|---|---|---|
| | | | Transfer agent according to the | Catalysts | | | | |
| Test n° | Water | Acrylic acid | invention* | $Na_2S_2O_8$ | $Na_2S_2O_5$ | $M_w$ | $I_p$ | $T_c$ |
| 20 | 400 | 400 | 77.5 | 4.68 | 1.336 | 14940 | 2.18 | >99 |
| 21 | 400 | 400 | 76.6 | 4.68 | 1.336 | 16120 | 2.18 | >99 |

$I_p$: polydispersity index
$M_w$: molecular weight (g/mole)
$T_c$: conversion rate (%)
*the transfer agent mass corresponds to the mass of an aqueous solution containing the said transfer agent, where the latter is diluted to 22% by weight.

Table 3 shows that the sulphurous transfer agent according to the invention enables one to obtain, according to the process according to the invention, homopolymers of acrylic acid:

having a polydispersity index lower than 2.2 determined in aqueous media by a gel permeation chromatographic (GPC) method having as a standard a series of 5 sodium polyacrylate standards supplied by Polymer Standard Service as references PAA 18K, PAA 8K, PAA 5K, PAA 4K and PAA 3K;

having a molecular weight of between 1000 g/mole and 20 000 g/mole;

and having a conversion rate higher than 99%.

EXAMPLE 5

The purpose of this example is to illustrate the use according to the invention of sulphurous compounds in a controlled radical polymerisation process of the RAFT type, in water, and using a batch process, of homopolymers of acrylic acid.

For tests n° 22 to n° 27, one starts by introducing, into a 2-liter reactor fitted with a mechanical stirrer and heating of the oil bath type, water and an aqueous solution containing the sulphurous transfer agent which is compound A obtained in test n° 1.

Whilst stirring, the bath holder bottom is then heated to a temperature equal to 95° C.

Keeping this temperature constant at ±2° C., one adds, during a period of 1 hour and using peristaltic pumps, the acrylic acid and the catalysts (4,4' azobis(4-cyanopentanoic) sold by the company Aldrich under the name V501). The temperature is then kept constant at 95° C.±2° C. for 2 hours.

The solution obtained is neutralised with soda until pH=8.5. One then obtains a clear, slightly orangey solution, which is cooled to ambient temperature and which contains a homopolymer of acrylic acid according to the invention, neutralised by sodium.

Table 4 indicates the quantity (in grams) of the various products used, together with the molecular weight $M_w$ (in g/mole), the polydispersity index $I_p$ and the conversion rate $T_c$, measured for the polymers obtained, which parameters are determined according to the methods described above in the present application.

TABLE 4 homopolymers of acrylic acid according to the invention

| | | Constituents (masses in grams) | | | Properties of the homopolymers according to the invention | | |
|---|---|---|---|---|---|---|---|
| | | | Transfer agent according to the | | | | |
| Test n° | Water | Acrylic acid | invention* | Catalyst (V501) | $M_w$ | $I_p$ | $T_c$ |
| 22 | 300 | 100 | 173 | 4 | 1540 | 1.5 | >99 |
| 23 | 300 | 100 | 138.4 | 3.2 | 1730 | 1.53 | >99 |
| 24 | 300 | 100 | 103.8 | 2.4 | 2155 | 1.55 | >99 |
| 25 | 300 | 100 | 69.2 | 1.6 | 2830 | 1.54 | >99 |
| 26 | 300 | 100 | 51.9 | 8.51 | 3730 | 1.59 | >99 |
| 27 | 150 | 50 | 17.3 | 8.01 | 5600 | 1.52 | >99 |

$I_p$: polydispersity index
$M_w$: molecular weight (g/mole)
$T_c$: conversion rate (%)
V501: 4,4'azobis (4-cyanopentanoic) sold by the company Aldrich under the name V501
*the transfer agent mass corresponds to the mass of an aqueous solution containing the said transfer agent, where the latter is diluted to 22% by weight.

Table 3 shows that the sulphurous transfer agent according to the invention enables one to obtain, using the process according to the invention, homopolymers of acrylic acid:

having a polydispersity index lower than 2.2 determined in aqueous media by a gel permeation chromatographic (GPC) method having as a standard a series of 5 sodium polyacrylate standards supplied by Polymer Standard Service as references PAA 18K, PAA 8K, PAA 5K, PAA 4K and PAA 3K;

having a molecular weight of between 1000 g/mole and 20 000 g/mole and in this example of between 1000 g/mole and 6 000 g/mole;

and having a conversion rate higher than 99%.

EXAMPLE 6

The purpose of this example is to illustrate the use according to the invention of a sulphurous compound according to the invention in a process for controlled radical polymerisation of the RAFT type, in water, of copolymers of acrylic acid with water-soluble monomers.

For tests n° 28 to n° 32, one starts by introducing, into a 2-liter reactor fitted with a mechanical stirrer and heating of the oil bath type, water and an aqueous solution containing the sulphurous transfer agent according to the invention which is compound A obtained in test n° 1.

Whilst stirring, the bath holder bottom is then heated to a temperature equal to 50° C. Keeping this temperature constant at ±2° C., one adds, for 2 hours and using peristaltic pumps, the acrylic acid, the water-soluble monomers and the catalysts (sodium persulphate and metabisulphite, respectively $Na_2S_2O_8$ and $Na_2S_2O_5$).

The temperature is then kept constant at 50° C.±2° C. for 1 hour.

The temperature is then increased to 95° C. and the solution is neutralised with soda until pH=8.5. One then obtains a clear, slightly orangey solution, which is cooled to ambient temperature and which contains a copolymer of acrylic acid with water-soluble monomers, neutralised by sodium.

Table 5 indicates the quantity (in grams) of the various products used, together with the molecular weight $M_w$ (in g/mole), the polydispersity index $I_p$ and the conversion rate $T_c$, measured for the copolymers obtained, which parameters are determined according to the methods described above in the present application.

EXAMPLE 7

The purpose of this example is to illustrate the use according to the invention of a sulphurous compound in a process for controlled radical polymerisation of the RAFT type, in water, of copolymers of acrylic acid with water-soluble monomers.

For tests n° 33 to n° 35, one begins by introducing, into a 1-liter reactor fitted with a mechanical stirrer and heating of the oil bath type:

346 grams of an aqueous solution 50% by weight of dry monomer of methoxy polyethyleneglycol methacrylate of molecular weight 5000 g/mole;

30 grams of acrylic acid;

a given quantity of the sulphurous transfer agent of formula A obtained in test n° 1 (tests n° 33 to n° 35 use respectively 6.3 grams, 12.6 grams and 25.2 grams of the said transfer agent).

TABLE 5 copolymers of acrylic acid with water-soluble monomers according to the invention

| | Constituents (masses in grams) | | | | | | Properties of the copolymers according to the invention | | |
|---|---|---|---|---|---|---|---|---|---|
| Test n° | Water | Acrylic acid | Water-soluble monomer | Transfer agent according to the invention* | Catalysts | | $M_w$ | $I_p$ | $T_c$ |
| | | | | | $Na_2S_2O_8$ | $Na_2S_2O_5$ | | | |
| 28 | 200 | 100 | 100 (AMA) | 69.2 | 1.755 | 0.501 | 7620 | 1.94 | >99 |
| 29 | 200 | 140 | 120 (acrylamide) | 69.2 | 1.755 | 0.501 | 5900 | 1.53 | >99 |
| 30 | 200 | 180 | 26.7 (MADQUAT) | 69.2 | 1.755 | 0.501 | 5350 | 1.42 | >99 |
| 31 | 200 | 170 | 30 (HEMA) | 69.2 | 1.755 | 0.501 | 5975 | 1.56 | >99 |
| 32 | 200 | 190 | 10 (AMPS) | 69.2 | 1.755 | 0.501 | 5330 | 1.45 | >99 |

$I_p$: polydispersity index
$M_w$: molecular weight (g/mole)
$T_c$: conversion rate (%)
AMA: methacrylic acid
AMPS: 2-acrylamido 2-methyl 1-propane sulphonic acid
MADQUAT: trimethylammonium ethyl chloride methacrylate
HEMA: ethylene glycol methacrylate
*the transfer agent mass corresponds to the mass of an aqueous solution containing the said transfer agent, where the latter is diluted to 22% by weight.

Table 5 shows that the sulphurous transfer agent according to the invention enables one to obtain, using the process according to the invention, copolymers of acrylic acid with water-soluble monomers:

having a polydispersity index lower than 2.2 determined in aqueous media by a gel permeation chromatographic (GPC) method having as a standard a series of 5 sodium polyacrylate standards supplied by Polymer Standard Service as references PAA 18K, PAA 8K, PAA 5K, PAA 4K and PAA 3K;

having a molecular weight of between 1000 g/mole and 20000 g/mole;

and having a conversion rate higher than 99%.

Whilst stirring, the bath holder bottom is heated to a temperature equal to 70° C., and an aqueous solution is introduced consisting of:

0.8 gram of $(NH_4)_2S_2O_8$;

10 grams of water;

It is left to react for 2 hours whilst maintaining the temperature at 82±2° C.

The solution obtained is then neutralised with soda until pH=7.1. One then obtains a solution which is cooled to ambient temperature and which contains a copolymer of acrylic acid with water-soluble monomers, neutralised by sodium.

Table 6 indicates the molecular weight $M_w$ (in g/mole), the polydispersity index $I_p$ and the conversion rate $T_c$, measured for the copolymers obtained, which parameters are determined according to the methods described above in the present application.

TABLE 6 copolymers of acrylic acid with water-soluble monomers according to the invention

| Test n° | Parameters of the copolymers according to the invention obtained by a polymerisation process according to the invention | | |
|---|---|---|---|
| | $M_w$ | $I_p$ | $T_c$ |
| 33 | 29470 | 1.44 | >99 |
| 34 | 52300 | 1.45 | >99 |
| 35 | 99500 | 1.67 | >99 |

$I_p$: polydispersity index
$M_w$: molecular weight (g/mole)
$T_c$: conversion rate (%)

Table 6 shows that the sulphurous transfer agent according to the invention enables one to obtain, using the process according to the invention, copolymers of acrylic acid with water-soluble monomers according to the invention:
having a polydispersity index lower than 2.2 determined in aqueous media by a gel permeation chromatographic (GPC) method having as a standard a series of 5 sodium polyacrylate standards supplied by Polymer Standard Service as references PAA 18K, PAA 8K, PAA 5K, PAA 4K and PAA 3K
having a molecular weight of between 1000 g/mole and 100,000 g/mole,
and having a conversion rate higher than 99%.

EXAMPLE 8

The purpose of this example is to present the synthesis of a new compound according to the invention, the chemical structure of which is in accordance with formula (I).

The purpose of this example is to illustrate the use of this compound according to the invention, in a process according to the invention of controlled radical polymerisation process of the RAFT type, in water, of a homopolymer of acrylic acid.
Test n° 36
Preparation of compound B of formula (I):

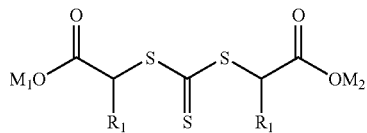

where $R_1$ designates the alkyl radical having 6 carbon atoms;
and $M_1$ and $M_2$ designate the sodium atom Na.
In a beaker being stirred by magnetic means, the following are weighed:
30.4 grams of water;
9.9 grams of 2 bromo-octanoic acid.
The mixture is neutralised with a 50% soda solution until a pH equal to 6.5 is obtained. The temperature rises to 50° C. A homogeneous solution is the obtained, which is cooled to 40° C.
13.7 grams of an aqueous solution of 25% disodic thiocarbonate solution is then poured drop by drop during a 20-minute period.

It is left to react for 2 hours, under stirring action. The alkylation S reaction is slightly exothermic and the temperature increases to 43° C., while the pH settles at 11.5.
A yellow paste is obtained containing compound B.
Test n° 37
In a 1-liter reactor fitted with a mechanical stirrer and heating of the oil bath type, the following is introduced:
300 grams of water;
100 grams of acrylic acid;
23.53 grams of an aqueous solution at 17.1% (by dry weight of polymer) containing compound B obtained according to test n° 36;
0.8 grams of a polymerisation initiator which is 4,4' azobis (4-cyanopentanoic) sold by the company Aldrich™ under the name V501.
Whilst stirring, the mixture is heated to a temperature equal to 100° C. The temperature is then maintained at 95° C. for 2 hours. A clear, slightly orangey solution is then obtained, which is cooled to ambient temperature.
This solution is neutralised with soda until pH=8.5; one then obtains a solution which contains a homopolymer of acrylic acid neutralised by sodium, of molecular weight equal to 13240 g/mole, with a polydispersity index equal to 1.83 and a conversion rate higher than 99% (these latter magnitudes are measured according to the methods previously described).

The invention claimed is:
1. Process for manufacturing in water a compound having a chemical structure in accordance with the following formula (I):

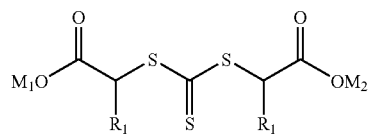

where $R_1$ designates an alkyl radical having 2 to 10 carbon atoms, and/or an aromatic radical optionally substituted by an alkyl chain having 1 to 4 carbon atoms;
and where $M_1$ and $M_2$ designate a hydrogen atom, an amine salt, ammonium, sodium, lithium or potassium, and are identical or different, comprising:
a) bringing into contact by pouring an aqueous solution of disodic trithiocarbonate $Na_2CS_3$ or an aqueous solution of dipotassic trithiocarbonate $K_2CS_3$ on a solution of a halogenated salt, which salt has a chemical structure in accordance with the following formula (II):

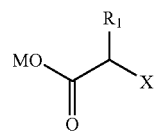

where $R_1$ designates an alkyl radical having 2 to 10 carbon atoms, or an aromatic radical optionally substituted by an alkyl chain having 1 to 4 carbon atoms;

where M designates a hydrogen atom, an amine salt, ammonium, sodium, lithium or potassium;

where X designates a halogen; and b) acidification of the resulting compound after step a).

2. A process according to claim 1, wherein the alkaline cations are selected from the group consisting of sodium, potassium and lithium.

3. A process according to claim 1, wherein $R_1$ is an alkyl radical having 2 to 6 carbon atoms, and M designates sodium or potassium.

4. A process according to claim 3, wherein $R_1$ is an alkyl radical having 2 to 4 carbon atoms, and M designates sodium or potassium.

5. A process according to claim 4, wherein $R_1$ is an alkyl radical having 4 carbon atoms, and M designates sodium or potassium.

6. A process according to claim 5, wherein $R_1$ is an alkyl radical having 4 carbon atoms, and M designates sodium.

7. A process according to claim 1, wherein X designates bromine.

* * * * *